United States Patent [19]

Sutter et al.

[11] Patent Number: 5,078,605

[45] Date of Patent: Jan. 7, 1992

[54] DEVICE FOR THE TREATMENT OF A BONE, PARTICULARLY A JAW BONE, AND/OR TOOTH

[75] Inventors: Franz Sutter, Niederdorf; Alexander Frei, Holderbank; Andreas E. Schwammberger, Seltisberg, all of Switzerland

[73] Assignee: Institut Straumann AG, Waldenburg, Switzerland

[21] Appl. No.: 445,401

[22] Filed: Dec. 4, 1989

[30] Foreign Application Priority Data

Dec. 2, 1988 [CH] Switzerland ............... 4486/88

[51] Int. Cl.$^5$ .................................................. A61C 3/02
[52] U.S. Cl. ..................................... 433/165; 433/82; 433/104; 408/59
[58] Field of Search ............... 433/82, 104, 165, 127, 433/128, 133, 147; 408/56, 59

[56] References Cited

U.S. PATENT DOCUMENTS

| 3,624,905 | 2/1970 | Barsby .................... 433/82 |
| 4,021,917 | 5/1977 | Nakanishi ............... 433/165 |
| 4,268,197 | 5/1981 | Burgsmuller ........... 408/59 |
| 4,693,646 | 9/1987 | Andrews ................. 408/59 |
| 4,749,316 | 6/1988 | Hendricks ............... 408/59 |

FOREIGN PATENT DOCUMENTS

| 2355961 | 5/1974 | Fed. Rep. of Germany ........ 433/82 |
| 2948682 | 6/1981 | Fed. Rep. of Germany . |
| 2949556 | 6/1981 | Fed. Rep. of Germany . |
| 3433570 | 3/1986 | Fed. Rep. of Germany . |
| 657807 | 9/1986 | Switzerland . |
| 1366638 | 9/1974 | United Kingdom .................. 408/59 |

OTHER PUBLICATIONS

"Orale Implantologie", pp. 66-71, 118-151, 178-243, Andre Schroeder et al.

*Primary Examiner*—John G. Weiss
*Attorney, Agent, or Firm*—Toren, McGeady & Associates

[57] ABSTRACT

The device comprises a tool 21 with a cutting part 23 and a shaft 25. The shaft 25 is provided with an annular catch groove 25d and carries a sleeve 31 which encloses it and comprises a catch projection 31c which engages in the catch groove 25d so as to be detachable, wherein the shaft 25 and the sleeve 31 are rotatable relative to one another. The sleeve 31 is provided with a coolant inlet 31d which opens into an annular duct 41 enclosing the shaft 25 and communicating with a passage 43. This duct 41 is connected with the passage 43 for guiding a coolant, which passage 43 extends through the tool 21 until its cutting part 23 and opens into the surroundings at the free end of the cutting part 23 or in the vicinity of the latter. The sleeve 31 can be secured against axial displacements by means of a catch projection 31c, which is engaged in a catch groove 25d, without separate connection parts and without taking up much axial space.

23 Claims, 2 Drawing Sheets

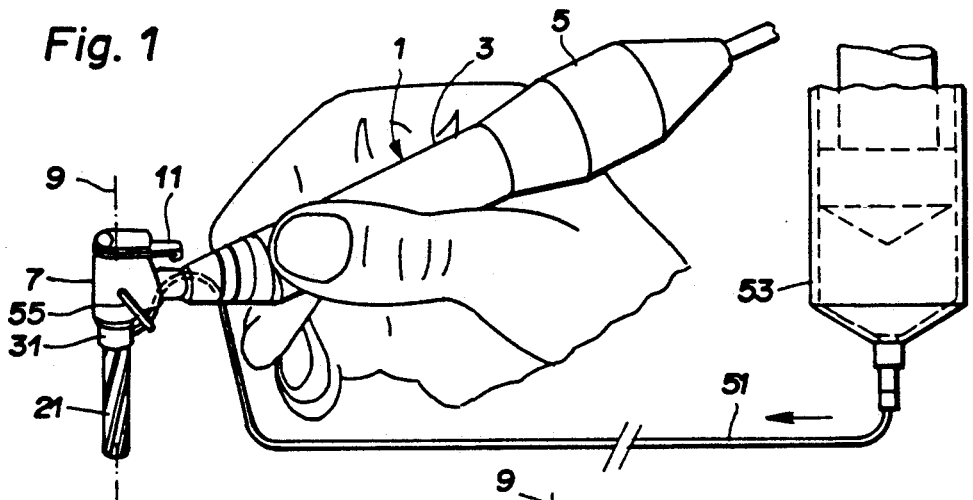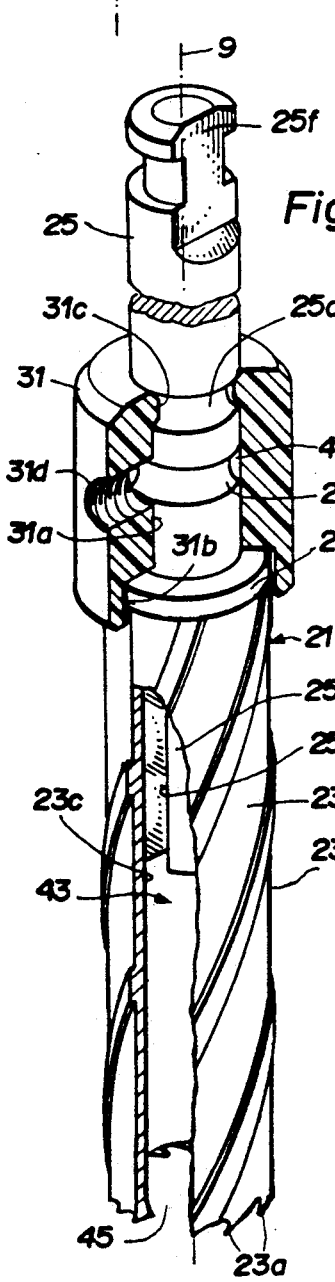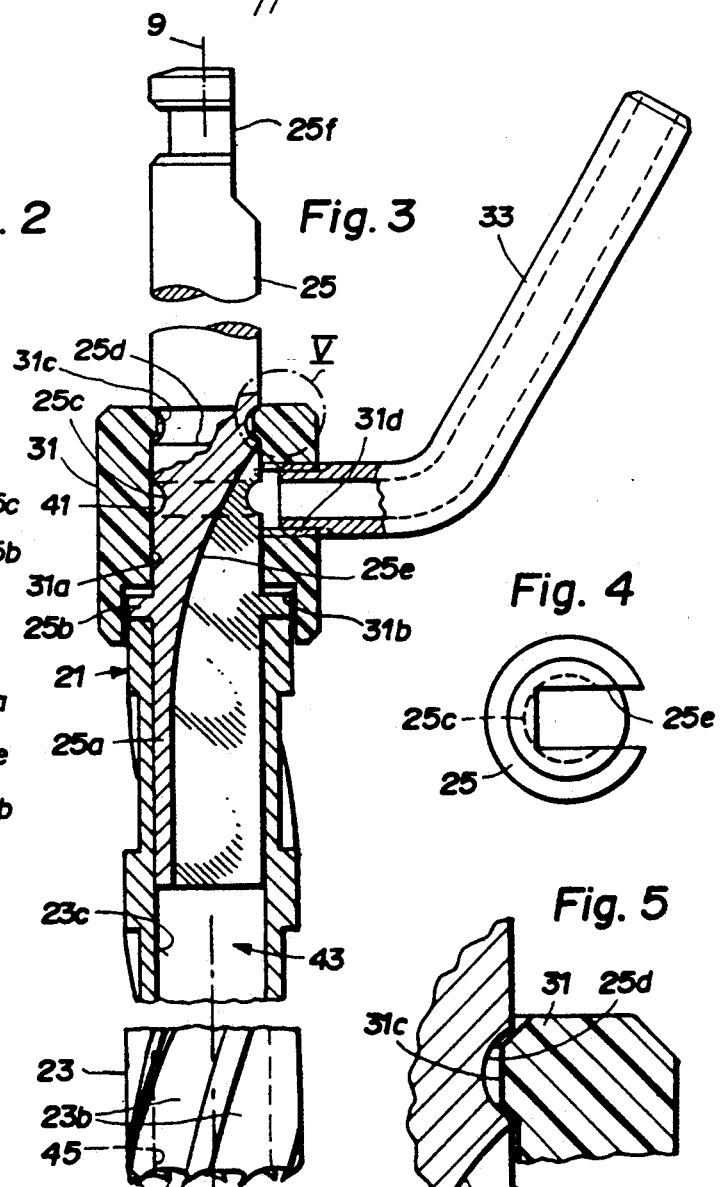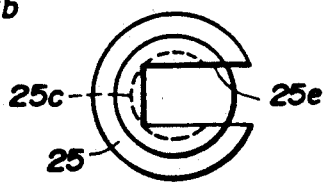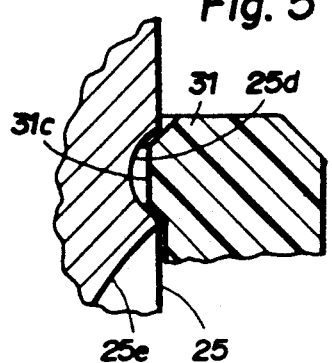

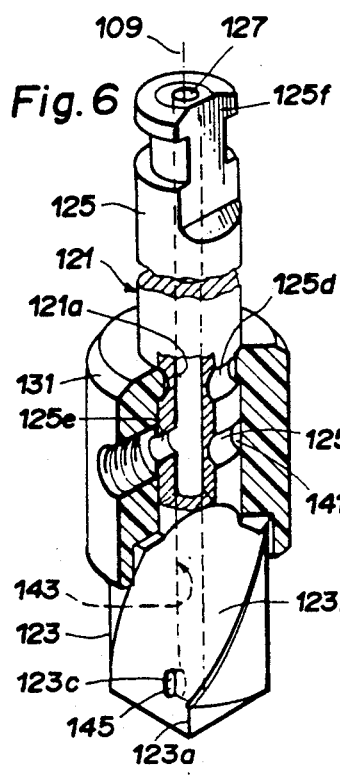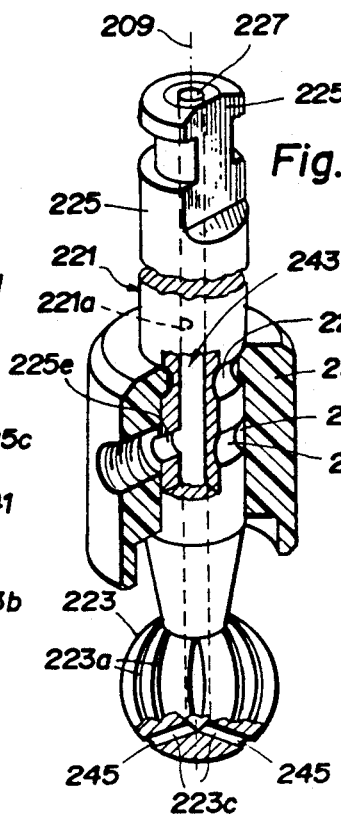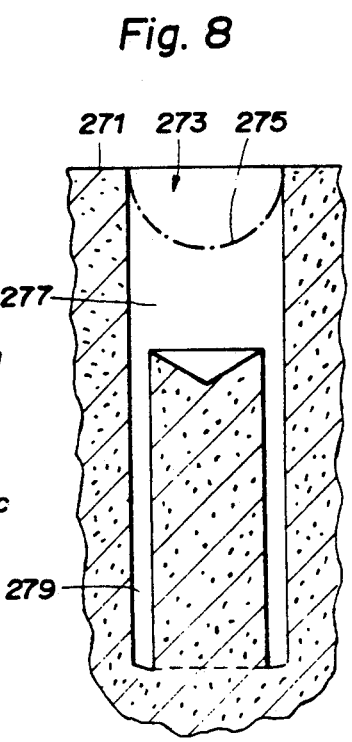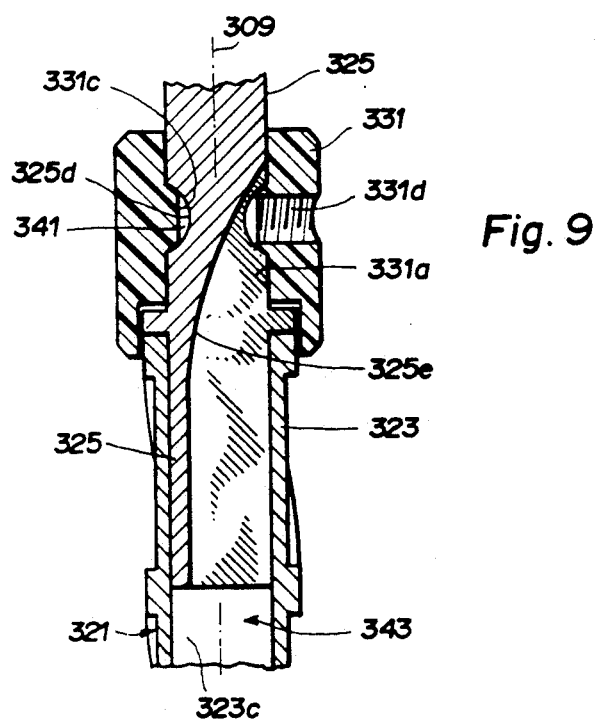

DEVICE FOR THE TREATMENT OF A BONE, PARTICULARLY A JAW BONE, AND/OR TOOTH

DESCRIPTION

This invention relates to a tool or device for use in dentistry. In particular, the invention relates to a device for the treatment of a bone, particularly a jaw bone, and/or a tooth, and is intended chiefly to provide a jaw bone with at least one hole in which an implant can be anchored for fastening a dental prosthesis, such as an artificial tooth or a set of teeth.

BACKGROUND OF THE INVENTION

Implants for the aforementioned purpose are known, e.g. from U.S. Pat. Nos. 4,180,910, 4,447,209 and from the book *Oral Implantology* [*Orale Implantologie*], André Schroeder, Franz Sutter and Gisbert Krekeler, Georg Thieme Verlag [publisher], Stuttgart, New York, 1988, title page and pages 66-71, 118-151, 178-187, 202-217, 228-243. These implants comprise a base or anchor comprising at least one hollow cylindrical part, which base is intended for insertion in a jaw bone. In order to anchor an implant in a jaw bone, the latter is provided with a hole for the hollow cylindrical part of the base or for each hollow cylindrical part of the base, respectively. Depending on the type and dimensioning of the implant, this hole can comprise e.g. an outer portion formed by means of a full bore hole, i.e. one which is hollow across its entire diameter, and a base or inner portion formed by means of an annular groove or kerf or can consist exclusively of a full bore hole or can consist exclusively of an annular groove and can possibly also be provided with an internal thread. In the aforementioned book, tools are also disclosed for producing holes in jaw bones. Heating above a maximum temperature of approximately 45° C. to 47° C. should be avoided in order that the bone material adjoining the holes does not die when producing the holes. As is likewise mentioned in the aforementioned book, the tools can be cooled with a liquid coolant, e.g. an aqueous, sterile, normal saline solution or Ringer's solution, which can be supplied e.g. to the outside of the tools, according to the book, in order to prevent excessive heating.

A device known from DE-C-3 433 570 comprises a rotatable tool with two pieces which can be screwed together so as to be detachable. One of these pieces forms a cutting part as well as a shoulder provided with an internal thread, and the other piece forms the shaft or—more precisely—at least its main part. The piece of the tool forming the main part of the shaft comprises an external thread, which is screwed together with the aforementioned internal thread, a collar and an annular groove on its side remote of the cutting part. The tool comprises a passage which makes it possible for it to be cooled on the inside with a liquid coolant. This passage comprises an axial hole, which extends from the front side at the free end of the cutting part at least until the annular groove, and a radial bore hole connecting the axial hole with the annular groove. A sleeve, which serves to feed the coolant to the tool and encloses the shaft in the area of the annular groove, is held so as to be rotatable and axially displaceable between the collar of the shaft and a separate adjusting ring fastened at the shaft. The sleeve is sealed with a sealing ring against the collar and the adjusting ring in each instance, and, together with the annular groove of the shaft, defines an annular duct and is provided with a coolant inlet opening into the latter.

Since the screwed-together threads of the two pieces of the tool must have a certain minimum length and since the adjusting ring also has a certain axial dimensioning, the tool is necessarily comparatively long and, in particular, longer than a tool comprising an identical cutting part constructed in a conventional manner, i.e. without inner cooling. The comparatively long length of the tool known from DE-C-3 433 570 impedes the dental treatment which is effected by means of the tool, particularly the treatment effected in the area of the molars. DE-C-3 433 570 contains no description as to how the adjusting ring is fastened. In commercially known devices constructed in general according to this publication, the adjusting ring is pressed on to the shaft, i.e. by means of a press-fit connection, so that it is not possible in practice for a dentist or his assistant to remove the sleeve from the shaft and mount it again on the latter. The tool and the sleeve must therefore be cleaned and sterilized in the assembled state before using, which makes it difficult to clean and sterilize satisfactorily. In addition, the device is comparatively expensive to manufacture because of the great number of parts to be produced and connected with one another.

SUMMARY OF THE INVENTION

The invention therefore has the object of providing a device which overcomes the disadvantages of the device known from DE-C-3 433 570 and the commercially known devices constructed in general according to this publication and, in particular, makes it possible to connect the sleeve with the tool without an adjusting ring or other separate connecting means which take up space in the axial direction, and, preferably, so as to be easily removable, wherein the device can be produced in an economical manner.

This object is met in accordance with one aspect of the invention by means of a device comprising a sleeve which is mounted to the device by means that substantially prevent displacement of the sleeve with respect to the cutting part of the device while allowing relative rotation between the sleeve and the cutting part.

In accordance with a further aspect of the invention, the connection means between the sleeve and the device comprises cooperating catch or latch means on the sleeve and on the device shaft.

In accordance with still another aspect of the invention, the sleeve mounting is such that the sleeve can be readily detached from the device.

In accordance with still a further feature of the invention, the sleeve mounting is such that, despite relative rotation and ready detachment, coolant supplied to the sleeve for passage to the cutter is reasonably prevented from leaking from around the sleeve. In a preferred embodiment, the sleeve is configured such that any leakage that does occur is directed toward the cutter.

These and further objects, features, and advantages of the invention will be apparent from the detailed description that follows below.

BRIEF DESCRIPTION OF THE DRAWINGS

The subject matter of the invention is now explained in the following by means of several embodiment examples shown in the accompanying drawings, wherein:

FIG. 1 shows a simplified perspective view of a device in accordance with the invention for treating a jaw bone;

FIG. 2 shows an perspective view of the tool and the sleeve of the device, shown in FIG. 1, serving to introduce a coolant into the tool, in enlarged scale;

FIG. 3 shows an axial section through the tool and the sleeve of FIG. 2;

FIG. 4 shows a top view of the front side of the tool forming the shaft of the concave or milling cutter, which front side is located at the bottom in FIG. 2;

FIG. 5 shows the section outline V from FIG. 3 of the catching means of the tool with the sleeve, in enlarged scale;

FIG. 6 shows a perspective view of another tool and a sleeve in accordance with the invention;

FIG. 7 shows a perspective view of still another tool and a sleeve in accordance with the invention;

FIG. 8 shows a section through a part of a jaw bone with a hole; and

FIG. 9 shows an axial section through a portion of a tool and a sleeve in accordance with the invention with other catch means.

DETAILED DESCRIPTION OF PREFERRED EMBODIMENTS

The device for treating a jaw bone shown in FIG. 1 comprises a drive device 1 with a handpiece 3 which is provided with an electric or pneumatic motor 5, an angle piece or contraangle 7 and a multiple-part housing. An angular gear unit comprising an output drive element which is rotatable around an axis 9 is arranged in the housing or housing part belonging to the angle piece 7. The angle piece 7 further comprises locking and/or coupling means with a manually swivelable actuating lever 11. A tool 21 in accordance with the invention, which is rotatable around the axis 9, is detachably and rigidly connected, i.e. coupled, with the output drive element by means of the locking and/or coupling means, wherein the connection or coupling can be locked and unlocked again by means of swiveling the actuating lever 11.

The tool 21, which is shown in FIGS. 2 and 3 in the state in which it is separated from the drive device 1, is generally symmetrical with respect to rotation relative to the axis 9 and comprises a cutting part 23 as well as a shaft 25. In the tool 21, which is constructed as a hollow-front cutter, the cutting part 23 and the shaft 25 are formed in each instance from an originally separate body, i.e. work piece, and are rigidly, undetachably and tightly connected with one another by means of welding. The cutting part 23 comprises a generally cylindrical sleeve and, at its free end, comprises a plurality of knife edges 23a, namely eight knife edges 23a, which are distributed along its circumference, as well as a plurality of clearance or clamping grooves 23b, namely four, extending along helical lines on its outer surface area, and an axial continuous hole or bore 23c in the central cross-sectional area. The workpiece forming the shaft 25 has an end portion 25a at its end on the cutting part side, which end portion 25a projects into the hole 23c, and an annular enlarged portion 25b forming a collar which divides the end portion 25a from the rest of the main part of the shaft, projects outward in the radial direction and contacts the end annular face of the cutting part 23 remote of the cutting edges.

The main part of the shaft 25 ending at the enlarged portion 25b on the side remote of the cutting part 23 comprises two grooves which annularly enclose the axis 9 and are arc-shaped shaped in axial section; the groove which is located closer to the enlarged portion 25b is designated by 25c and the other groove serves as a catch groove 25d. In addition, the shaft 25 is provided with a notch 25e extending in the axial direction. This notch 25e extends from a starting point, which is located on the side of the groove 25c remote of the cutting part 23 and approximately between the groove 25c and the catch groove 25d and/or in the vicinity of the rim of the latter on the cutting part side, until the end face of the end of the shaft 25 located in the hole 23c of the cutting part 23. The base of the notch 25e is inclined relative to the longitudinal direction of the tool, at least in its starting portion remote of the cutting part 23, in such a way that its radially measured depth increases toward the free end of the cutting part 23 provided with the knife edges 23a. That is, the base of the notch 25e has a portion which is curved in a concave manner in axial section and begins at said starting point of the notch on the outer surface area or circumferential area of the shaft. A portion which is parallel to the axis 9 and extends until the end of the workpiece forming the shaft, which end is arranged in the hole 23c of the cutting part 23, adjoins the curved portion of the notch base in a continuous manner. The notch 25e, as shown in FIG. 4, is rectangular in cross section. At its end remote of the cutting part 23, the shaft is provided with a coupling portion 25f which, in order to connect the tool 21 with the output drive element of the angle piece 7 so that they are fixed with respect to rotation relative to one another, comprises a flattened portion, which is parallel to the axis 9, and an arc-shaped groove which opens into the flattened portion at both ends and serves for the axial locking of the tool in the angle piece.

A sleeve 31 having an axial, continuous hole 31a is supported on the longitudinal portion of the shaft located between the cutting part 23 and the coupling portion 25f. This hole 31a comprises a widened portion 31b at the end on the cutting part side, which widened portion 31b receives the enlarged portion 25b and accordingly also the shoulder formed by the latter on the side remote of the cutting part 23, as well as the cutting part end remote of the knife edges 23a. The inner surface of the sleeve 31 defining the hole 31a is provided, in the vicinity of its end remote of the cutting part 23, with an annular rib which projects radially toward the axis 9; the rib forms a catch projection 31c and defines a portion of the hole 31a which is reduced in diameter. As is shown particularly clearly in FIG. 5, the catch projection 31c projects into the catch groove 25d and has inclined flanks which approach one another in the direction toward the groove base. The shaft 25 and the sleeve 31 are constructed in such a way that they are rotatable around the axis 9 with slight, radial play relative to one another in a favorable and easy manner, i.e. with only slight friction. The catch groove 25d and the catch projection 31c, together with the remaining part of the shaft 25 and the sleeve 31, respectively, form in the body catch means 25d, 31c, integral with their associated body part, which catch means 25d, 31c secure the sleeve 31, with respect to the shaft 25, against axial displacements directed away from the cutting part 23 as well as against axial displacements directed toward the cutting part 23 and thus hold the sleeve at the tool in such a way that it is not displaceable axially—with the exception of a slight axial play which is present in any case—but is detachable. The jacket of the sleeve 31 is provided, in the area of the groove 25c of the shaft 25, with a coolant inlet 31d, namely a radial threaded bore hole, which opens into the axial opening 31a from the outside. An angled or bent pipe piece, which comprises a portion which is inclined away from the radial notch 31d and from the cutting part 23 with respect to the axis 9 and serves as a connection 33, is screwed into this threaded bore hole 31d.

The coolant inlet 31d opens into an annular duct 41 which encloses the shaft 25 and is defined by the sleeve 31 and the groove 25c of the shaft 25. This duct 41 is connected, with reference to fluid, with a vertically-extending passage 43 which is formed by the notch 25e of the shaft 25 and by the free part of the opening 23c of the cutting part 23 and which extends in a generally axial direction through a portion of the tool and opens into the surroundings at the free end of the cutting part with an outlet opening 45 formed by the end of the hole 31a. The connection 33 is connected with the output of a coolant feed or supply device 53 by means of a flexible tube which is placed on the connection 33 and serves as coolant feed line 51; the coolant feed device 53 comprises a syringe with a generally cylindrical container or vessel and a piston which can be pressed into the latter manually via a shaft. The connection 33 and/or the feed line 51 can be held with a holder 55 at the angle piece 7 so as to be detachable. The holder 55 can be formed, e.g. by means of an approximately U-shaped or C-shaped stirrup or clip which is clipped on at the housing of the angle piece so as to be detachable.

The tool 21 consists of a metallic material, e.g. steel. The sleeve 31 comprises a thermoplastic plastic material. The latter should be constituted in such a way that the sleeve 31 is fixed with respect to shape, but is elastically deformable to a sufficient degree to enable an engagement and disengagement of the catch means 25d, 31c. Moreover, the inner surface of the sleeve defining the axial hole 31a should have good sliding or low friction characteristics. In order that the sleeve 31 can be sterilized by means of heating produced e.g. by hot water and/or hot steam, the component plastic should also be resistant to heat up to temperatures of at least 120° C. and preferably up to at least 180° C. or, and e.g. at least briefly, up to 200° C. or even up to at least 220° C. In addition, the sleeve, and also the tool 21, are to comprise a biologically compatible, nontoxic material. Finally, the plastic serving as a component should be capable of being processed easily and particularly extruded and/or injection molded. A plastic suitable for forming the sleeve 31 which fulfills the aforementioned requirements is e.g. polyether ether ketone (PEEK). The connection 33 can comprise e.g. a metallic material.

Since the sleeve 31 serving to feed the liquid coolant to the tool 21 and to introduce the coolant into the passage 43 of the tool 21 overlaps the enlarged portion 25b of the shaft 25 and even a small portion of the cutting part 23 in addition, it is located immediately behind the portion of the cutting part 23 usable for a bone treatment. The end of the output drive element of the angle piece 7 used for the insertion of the tool 21 comprises an annular, radial end face and projects e.g. a small distance out of the housing of the angle piece 7 and/or is approximately flush with the housing. When the tool 21, according to FIG. 1, is connected with the angle piece 7, the shaft 27 mounts into an axial hole of the output drive element. The sleeve 31 is located at least approximately immediately in front of the opening of the angle piece housing in which the output drive element and the shaft 25 exit from this housing. The sleeve 31 is separated from said end face of the output drive element which rotates during operation and/or from the housing of the angle piece by means of a narrow intermediate space which is shaped in the manner of an annular gap. Thus, the distance between the boundary of the angle piece 7 on the cutting part side and the end on the angle piece side of the portion of the cutting part 23 usable for the treatment of a jaw bone need be only very slightly larger than the dimensioning of the sleeve 31 measured in the axial direction. This dimensioning of the sleeve 3 is at most three times and e.g. approximately twice the diameter of the cylindrical main part of the shaft 25. The outer diameter of the main part of the shaft of the tool 21 serving for the treatment of the jaw bone can be e.g. approximately 2.35 mm. The axial dimensioning of the sleeve 31 can then be at most 7 mm and, e.g. approximately 5 mm. The length of the tool 21 and accordingly also the overall dimensioning of the angle piece 7 and tool 21 measured parallel to the axis 9 can therefore be relatively short, which is advantageous particularly in the treatment of a jaw bone in the area of the molars.

The annular duct 41 defined by the groove 25c of the shaft 25 and the sleeve 31 is first sealed relative to the surroundings of the sleeve 31 by means of the cylindrical surface portions of the outer surface area of the shaft 22 and of the inner surface of the sleeve 31, which cylindrical surface portions are supported on one another in pairs on both sides of the duct 41 with slight radial play. In addition, the shoulder which is formed by the enlarged portion 25b in the interior of the widened portion 31b of the hole 31a, together with the edge portion of the sleeve 31 enclosing the cylindrical circumferential surface area of the enlarged portion 25b with, at most, a slight radial play, form a labyrinth seal on the side of the duct 41 facing the cutting part 23, which labyrinth seal is approximately Z-shaped in axial section. On the side of the annular duct 41 remote of the cutting part, the duct 41 is additionally sealed by means of the catch projection 31c which projects into the catch groove 25d and comprises an annular rib that encloses the shaft completely and in a continuous uninterrupted manner. Thus, with the exception of the connection 33 screwed into the coolant inlet 31, the duct 41 is sealed relative to its surroundings exclusively by means of portions of the shaft 25 of the tool 21 and portions of the sleeve 31 so as to be more or less tight against liquid without the need or use of separate, rubber-elastic sealing rings.

FIG. 6 shows a modified tool 121 which is constructed as a spiral or twist drill, is rotatable around an axis 109 and comprises a cutting part 123 and a shaft 125, wherein the cutting part and the shaft in this tool comprise a coherent integral body in one piece. The tool 121 is provided with a coaxial hole 121a extending from the end face of the free shaft end to the vicinity of the free end of the cutting part 123, namely a cylindrical pocket bore hole. The hole 121a is tightly sealed at the end on the shaft side by means of a cylinder-shaped locking element 127 whose end portion is pressed in and/or welded in. The cutting part 123 has two knife edges 123 or—more exactly—main knife edges at its free end and two clearance or clamping grooves 123b in the area of its circumferential surface. In addition, the cutting part 123 comprises two holes 123c which form an angle with the axis 109, i.e. radial holes 123c or holes 123c which are inclined relative to the axis 109, and which open into one of the two clamping grooves 123b in each instance in the vicinity of the free end of the cutting part 123 from the end portion of the axial hole 121a. The diameter of the cutting part 123—or, more exactly, of the enveloping-circle cylinder of the cutting part—is greater than the diameter of the shaft 125, so that the end of the cutting part 123 on the shaft side, together with the shaft 125, at least in the circumferential areas not occupied by the clamping grooves, forms a shoulder with a radial surface in a manner analogous to the enlarged portion 25b of the shaft 25. The shaft 125 has an annular groove 125c and an annular catch groove 125d which are arranged and constructed in a manner analogous to the grooves 25c and 25d, respectively, of the shaft 25. In addition, the shaft 125 is provided with a hole 125e opening from the groove 125c into the axial hole 121a, namely a radial bore hole. The shaft 125 cutting part 123, which coupling portion 125f is constructed analogous to the coupling portion 25f.

A sleeve 131 is constructed in a manner identical to the sleeve 31 or is even formed by means of the sleeve 31 itself and is held at the shaft 125 in a manner analogous to the sleeve 31 at the shaft 25. The edge portion of the sleeve on the cutting part side overlaps the end portion of the cutting part 123, which adjoins the shaft 125 and forms an enlarged portion of the tool 121 with respect to the shaft 125, similar to the way the corresponding rim portion of the sleeve 31 forms the enlarged portion 25b of the shaft 25 and a short portion of the cutting part 23. Moreover, the sleeve 131 is provided with a connection, not shown, corresponding to the connection 33. Together with the groove 125c, the sleeve 131 defines an annular duct 141. Together with the radial hole 125e and the holes 123c, the free part of the axial hole 121a defines a passage 143 which comprises outlet openings 145 formed by the outer ends of the two holes 123c and opening into the surroundings in the area of the cutting part.

The tool 221, seen in FIG. 7, which is another modification, is rotatable around the axis 209 and comprises a spherical or, more exactly, spherical portion-shaped cutting part 223 and a shaft 225 which, e.g. together with the latter, comprises a body in one piece. The tool 221 comprises a hole 221a which is coaxial relative to the axis 209, namely a pocket bore hole which extends from the free end of the shaft 225 up to the vicinity of the tool end on the cutting part side and is sealed in the free shaft end by means of a locking or closing element 227. The cutting part 221 comprises a plurality of knife edges 223a, which are distributed along its circumference, and holes 223c which 209 and are inclined away from the latter and from the shaft. These holes 223c extend from the end of the axial hole 221a on the cutting part side into the hemispherical part of the outer surface area of the cutting part 223 remote of the shaft. The shaft 225 comprises a cylindrical main part which is connected, at its ends on the cutting part side, with the cutting part by means of a conical neck. The shaft 225 is provided with a groove 225c and a catch groove 225d which are arranged and constructed analogous to the grooves 25c and 25d, respectively. In addition, the shaft 225 comprises a radial hole 225e, which connects the groove 225c with the axial hole 221, and a coupling portion 225f.

A sleeve 231, which is constituted in a manner identical to the sleeve 31 or is formed by the sleeve 31 itself, is held on the shaft 221 so as to be relatively rotatable and detachable but not displaceable axially and, together with its groove 225c, defines an annular duct 241.

The free portion of the axial hole 221a, together with the radial hole 225e of the shaft 225 and the holes 223c of the cutting part 223 which are inclined relative to the axis 209, forms a passage 243 which opens into the surroundings when the outlet openings 245 are formed by the outer ends of the holes 223c.

The sleeves 131 and 231 are held on the shafts 125 and 225, respectively, in an analogous manner so as to be relatively rotatable and not displaceable axially, as was described for sleeves 31 and the shaft 25. In addition, the shafts of the three tools 21, 121, 221 have identically constructed coupling portions 25f, 125f, 225f, so that any one of the three tools, as desired, can be inserted into the angle piece 7 and rotated via its angle drive by means of the motor of the drive device 1. The cutting parts of the three tools 21, 121, 221 have e.g. at least approximately identical outer diameters. The device with the drive device 1 and the three tools 21, 121, 221 can be used for providing the bone 271, namely jaw bone 271, a section of which can be seen in FIG. 8, with a hole 273 for receiving an implant of the type described in the beginning. For this purpose, the tool 221 is first inserted into the angle piece 7 and a marking hole 275 indicated in dash-dot lines in FIG. 8 is arranged in the bone. The tool 121 is then inserted into the angle piece 7 and a pocket bore hole is drilled at the marking hole 275 in the bone with the tool 121, which pocket bore hole forms the cylindrical outer portion 277 of the hole 273, which outlet portion 277 is hollow across the entire diameter. Finally, the annular groove-shaped base or kerf portion 279 of the hole 273 is cut into the bone with the tool 21 proceeding from the conical base of the pocket bore hole.

Some operating characteristics of the device will now be mentioned, wherein the treatment of the jaw bone with the tool 21 is explained in more detail as an example. This tool 21 is rotated in the clockwise direction by means of the motor of the drive device 1 via the angle gear unit of the angle piece— seen from above in FIG. 1—when treating the bone. When the sleeve 31 is located on the shaft 25 of the tool 21 so as to be freely rotatable, the latter tends to rotate the sleeve 31 until the position in which the portion of the connection 33 which is inclined away from the cutting part 23 in an upward direction and/or the tube which is placed on the connection 33 and forms the feed line 33 contacts the side of the housing of the angle piece 7 located at the rear in FIG. 1. In addition, the connection 33 and/or the feed line 33 is/are held at the angle piece by means of the holder 55. The sleeve 31 is therefore held by means of the connection 33 and the feed line 51 in cooperation with the holder 55 so as to be non-rotatable with respect to the housing of the drive device, so that it is not rotated along with the tool. The fact that there are no separate, rubber-elastic sealing rings between the shaft 25 and the sleeve 31 contributes to the tool 21 and the sleeve 31 being favorably and easily rotatable, i.e. with low friction relative to one another. During the rotation of the tool taking place for the cutting of the base portion 279 of the hole, e.g. an assistant of the dentist or surgeon performing the treatment can actuate the feed device 53, i.e. can press its piston into the container and thereby feed the liquid coolant stored in the feed device, namely e.g. an aqueous solution with a temperature of approximately 5° C., through the feed line 51, the connection 33 and the sleeve 31 to the tool 21 and introduce it into its passage 43. The coolant can then flow through the passage 43 to the outlet opening 45, exit into the surroundings at the latter and cool the cutting part 23 and particularly its knife edge 23a and also the treated bone in the area of the treatment location. As described further above, the shaft 25 and the sleeve 31 close the annular duct 41 defined by them so as to be at least approximately tight with respect to fluid relative to the surroundings. At all events, at the rim of the sleeve 31 on the cutting part side, coolant which nevertheless exits or leaks between the latter and the circumferential surface of the tool is directed toward the free end of the cutting part 23 by means of the rim portion of the sleeve 31 overlapping the enlarged portion 25b, so that this coolant likewise contributes to the cooling of the tool and the treated bone area.

In the tools 121 and 221, the annular ducts 141 and 241, respectively, which are defined by their grooves 125c and 225c, respectively, and the sleeve 131 and 231, respectively, are sealed relative to the surroundings by means of portions of the tools and sleeves so as to be at least approximately tight with respect to liquid in a manner similar to the tool 21 and the sleeve 31. With respect to the tool 121 in which the cutting part 123 projects with slight radial play into the widened portion of the sleeve 131 corresponding to the widened portion 31b and the clamping grooves 123b extend up to the end portion of the sleeve 121 on the cutting part side, at all events in the end of the sleeve on the cutting part side, coolant which exits between the latter and the tool is mainly guided into the clamping grooves, where it likewise contributes to the cooling of the cutting part.

Every tool 21, 121, 221—as shown in FIGS. 1 to 3 and 5 to 7—can be equipped with a sleeve 31 and 131 and 231, respectively, which is assigned to it and held detachably on its shaft. When the tool required for a determined treatment phase is inserted into the angle piece 7, the tube forming the feed line 51 can be inserted on the connection of the respective sleeve. However, it is also possible to utilize one and the same sleeve, e.g. sleeve 31, for feeding the coolant to the three tools 21, 121, 221. In this case, when exchanging the tools, the sleeve 31 can be removed from the shaft of the previously used tool and inserted on the shaft of the tool to be used next. The sleeve can be removed effortlessly and quickly from the tool shaft holding it in that the sleeve is grasped with the hand or an instrument and a force directed away from the cutting part is exerted on it. Accordingly, the catch projection 31c of the sleeve can first be disengaged from the catch groove 25d of the respective tool and the sleeve can then be displaced upward (in FIG. 2) toward the free end of the shaft and removed from it. Subsequently, the sleeve can be inserted on the free shaft end of the tool to be used, likewise in an effortless and rapid manner, and pushed along the shaft in the direction of the cutting part until the catch means engage.

As can be seen from FIG. 8, the annular groove-shaped base portion 279 of the hole 273 encloses a bone core which is continuous with the rest of the bone and comprises bone material and subsequently projects into the interior of the hollow-cylindrical base part of the implant, not shown. However, in practice, when cutting the annular groove-shaped base portion 279 of the hole, it can happen occasionally that the bone core breaks off and remains in the hole 23c of the cutting part 23 of the tool 21. In such a case, the tool 21 can be withdrawn from the hole of the bone and separated from the angle piece. The sleeve 31 can then be removed from the shaft 25 of the tool and an elongated part of an extracting instrument, which e.g. can be bent slightly, but is suitable for transmitting the pressure forces, can then be inserted into the notch 25e and the broken off bone pin remaining in the cutting part 23 can be extracted from the cutting part in the direction away from the shaft 25. Subsequently, the sleeve 31 can be inserted again on the shaft 25, if necessary, and the hole in the bone can be finished.

The tools and sleeves are to be cleaned and sterilized after use and before using for the treatment of another patient. The sleeves can be removed from the tools for cleaning, so that a satisfactory cleaning is substantially facilitated. The sterilization of the tools and sleeves can be effected e.g. with hot water and/or steam at a temperature of at least approximately 120° C. and e.g. approximately 180° C. to 220° C., wherein the sleeves can be mounted on the tools or separated from them during sterilization.

The angle piece 7 is preferably provided with a nozzle, not shown, which is fastened at the outside of its housing in a known manner and which comprises an outlet opening directed against the circumferential surface of the cutting part of the tool and a connection for supplying a coolant. This nozzle enables the tools 21, 121, 221 to be cooled, in addition, by means of a coolant supplied through one of its passages 43, 143, 243 for internal cooling or, instead of this, a cooling of its outer sides. If the tools 21, 121, 221 are used without supplying a coolant to its passages 43 and 143 and 243, respectively, the sleeves can be removed from the tools, or at least the connection of the connections of the sleeves with the feed line 51 can be dispensed with.

FIG. 9 shows a part of a modified tool 321 which is rotatable around a axis 309 and comprises a cutting part 323 and a shaft 325 on which a sleeve 331 is held so as to be detachable. The cutting part 323 is constructed e.g. similar to or identical to the cutting part 23 and has an axial hole 323c. The shaft 325 has a notch 325e corresponding to the notch 25e. This notch 325e extends from the end of the shaft 325 located in the hole 323c until the shaft portion enclosed by the sleeve 331, specifically at least until the catch groove 325d The sleeve 331 comprises a catch projection 331c, which consists of an annular rib and projects into the catch groove 325d, and a coolant inlet 331d which opens into the axial hole 331a of the sleeve in the area of the catch projection and is formed by means of a radial threaded bore hole; a connection, not shown, which is constructed identically or similar to the connection 33 can be screwed into this radial threaded bore hole. The cross-sectional shapes and dimensioning of the catch groove 25d and the catch projection 331c are dimensioned in such a way that an annular duct 341 remains open between the groove base and the catch projection. This duct is connected with the passage 343 of the tool 321 formed by the hole 323c and the notch 325e. Thus, the tool 321 is distinguished from the tool 21 in that, instead of the two annular grooves 25c, 25d, only the catch groove 325d is present, which catch groove 325d serves for the detachable catching of the sleeve 331 as well as for forming the duct 341. Apart from this difference and the change in the sleeve for the purpose of adaptation, the tool 321 and the sleeve 331 are constructed in a manner similar to or identical with the tool 21 and the sleeve 31, respectively.

The devices according to the invention can be changed in other ways. In particular, features of the different tools and sleeves can be combined. For example, in the tools 121, 221, the two grooves 125c, 125d and 225c, 225d, respectively, can naturally also be replaced by a single groove which, in a manner analogous with the catch groove 325d, serves for the catching or latching of the sleeve as well as for defining an annular duct. The sleeves 131, 231 would then be constructed so as to be correspondingly identical or similar to the sleeve 331. Moreover, the shafts of the tool 121 and 221 could also be provided with an enlarged portion which is constructed and arranged correspondingly to the enlarged portion 25b of the shaft 25 and which can be received by the widened portion of the axial hole of the sleeve held on the respective shaft, which widened portion corresponds to the widened portion 31b. But it would also be possible to omit the collar defining the widened portion 31b of the sleeve 31, so that the sleeve 31 in FIGS. 2 and 3 extends only until the upper, annular radial surface of the enlarged portion 25b. The same applies for the sleeves of the other embodiment examples. In addition, the notches 25e, 325e of the shafts 25 and 325, respectively, could be replaced by an axial hole, which extends from the shaft end on the cutting part side up to the annular duct 41 or 341, and a radial hole connecting the axial hole with the groove 25c or the catch groove 225d, respectively.

The catch means could be constructed in such a way that they secure the sleeves only against displacements directed away from the cutting part of the respective tool and allow displacement in the opposite direction. Displacements of the sleeves directed toward the notch part could then be prevented by means of at least one shoulder and/or stop face of the tool projecting outward away from the axis, as formed in tool 21 by the enlarged portion 25b and in tool 121 by its cutting part adjoining the shaft.

Of course, the shapes and dimensioning of the tools can be changed in many ways corresponding to their purposes. In the tools 21, 321 in which the cutting part and the shaft are workpieces could be connected with one another in a rigid and undetachable manner by means of soldering or cementing connections instead of by welding connections. In addition, the tools can also be constructed for the treatment of teeth, so that in addition to the cutting part of a tool, the tooth area treated with the latter can also be cooled by means of the coolant. Moreover, the devices and their tools can also be provided for the treatment of other bones instead of upper and lower jaw bones and, in particular, to be provided with holes.

The free hollow space of the annular ducts enclosing the axes and shafts of the tools could be formed, instead, by means of a groove arranged in the outer surface area of the respective shaft or, in addition to this, by means of an annular groove arranged in the inner surface of the sleeve.

The various tools and sleeves can be inexpensively produced. Moreover, the sleeves can be assembled on the tools and separated from the tools quickly and simply. In so doing, it is particularly advantageous for production and assembly costs that no fastening parts or seals formed by separate workpieces are required in order to secure the sleeves on the tools against axial displacement and seal them.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A device for the treatment of a bone or a tooth, comprising a tool and a sleeve, said tool being rotatable around an axis and comprising a cutting part, and a shaft connected to the cutting part, said sleeve being arranged on the shaft and together with the latter defining an annular duct for coolant, said sleeve comprising a coolant inlet opening into the duct, said tool comprising a passage extending from the duct to the cutting part, mounting means including catch means for mounting the sleeve on the shaft such that the shaft is rotatable relative to the sleeve and that the sleeve is secured against displacements in both axial directions, said catch means comprising an annular catch groove provided in the shaft and a catch projection integral with the projecting from the sleeve into the catch groove and engaging same, wherein the catch means function to secure the sleeve against axial displacements in at least the direction away from the cutting part, said catch projecting comprising an annular rib which encloses the shaft completely and in a continuous manner, said annular duct for coolant being formed by an annular groove in the shaft, and wherein the catch groove and said rib forming the catch projection are located on the side of the duct remote of the cutting part.

2. The device of claim 1, wherein the sleeve is slightly resilient to allow ready detachment of the sleeve from the shaft.

3. The device of claim 1, wherein the sleeve is configured such that any coolant leakage is directed toward the cutter.

4. Device according to claim 1, wherein the engaged catch means can be disengaged by means of a force which is exerted on the sleeve with respect to the tool and directed away from the cutting part, the shaft being configured such that the sleeve after disengagement can be removed from the tool by means of displacement directed away from the cutting part.

5. Device according to claim 1, wherein the catch means is configured to secure the sleeve also against displacements directed toward the cutting part.

6. Device according to claim 1, wherein the annular duct is sealed relative to the surroundings of the tool and of the sleeve on its side facing the cutting part and on its opposite side solely by means of portions of the tool and of the sleeve.

7. Device according to claim 1, wherein the shaft and the cutting part are undetachably and rigidly connected and constituted of metal, and the sleeve is of plastic.

8. Device according to claim 7, wherein the shaft and cutting part are formed from the same piece of metal.

9. Device according to claim 7, wherein the shaft and cutting part are formed from different pieces of metal and are welded together.

10. Device according to claim 7, wherein the plastic is of a material which can be injection molded and is resistant to heat up to temperatures of at least 120° C.

11. Device according to claim 1, wherein the cutting part comprises a hollow slot-forming cutter, a twist drill, or a ball-shaped cutter.

12. Device according to claim 1, wherein the shaft diameter is less than that of the cutting part.

13. Device according to claim 1, wherein the portion of the passage being inside the cutting part consists at least in part of an axial hole.

14. Device according to claim 1, wherein said passage comprises an axial hole and a radial hole connecting said annular groove forming the annular duct with said axial hole.

15. A device for the treatment of a bone or a tooth, comprising a tool and a sleeve, said tool being rotatable around an axis and comprising a cutting part, and a shaft connected to the cutting part, said sleeve being arranged on the shaft and together with the latter defining an annular duct for coolant, said sleeve comprising a coolant inlet opening into the duct, said tool comprising a passage extending from the duct to the cutting part, means for mounting the sleeve on the shaft such that the shaft is rotatable relative to the sleeve and the sleeve is secured against displacements at least in a direction away from the cutting part, said mounting means comprising cooperating catch means present at the shaft and at the sleeve and which engage with one another, the tool passage comprising an axial hole with an outlet opening into the free end of the cutting part, and the shaft comprising an axially extending notch which connects the annular duct with the axial hole of the passage, the inner surface of the notch having a portion opposed to the coolant inlet opening that is inclined relative to the longitudinal direction of the tool such that its radially measured depth increases toward the free end of the cutting part.

16. Device according to claim 15, wherein the shaft notch is covered relative to its surroundings at least in part by means of the sleeve.

17. Device according to claim 15, wherein the shaft notch is covered relative to its surroundings at least in part by means of the cutting part.

18. Device according to claim 15, wherein the cutting part and the shaft are formed from originally separate workpieces.

19. Device according to claim 18, wherein the workpiece forming the shaft projects into the workpiece forming the cutting part.

20. Device according to claim 19, wherein the notch extends until the end of the workpiece forming the shaft on the cutting part side.

21. A device for the treatment of a bone or a tooth, comprising a tool and a sleeve, said tool being rotatable around an axis and comprising a cutting part, and a shaft connected to the cutting part, said sleeve being arranged on the shaft and together with the latter defining an annular duct for coolant, said sleeve comprising a coolant inlet opening into the duct, said tool comprising a passage extending from the duct to the cutting part, means for mounting the sleeve on the shaft such that the shaft is rotatable relative to the sleeve and the sleeve is secured against displacements at least in a direction away from the cutting part, said mounting means comprising cooperating catch means present at the shaft and at the sleeve and which engage with one another, the annular duct being sealed relative to the surroundings of the tool and of the sleeve on its side facing the cutting part and on its opposite side solely by means of portions of the tool and of the sleeve, the sleeve further comprising an axial, continuous bore having a widened portion at its end of the cutting part side and surrounds the tool, said tool further comprising a shoulder n the side of the annular duct facing the cutting part, said shoulder being formed by an enlarged portion of the shaft and being located inside the sleeve widened portion.

22. A device for the treatment of a bone or a tooth, comprising a tool and a sleeve, said tool being rotatable around an axis and comprising a cutting part, and a shaft connected to the cutting part, said sleeve being arranged on the shaft and together with the latter defining an annular duct for coolant, said sleeve comprising a coolant inlet opening into the duct, said tool comprising a passage extending from the duct to the cutting part, means for mounting the sleeve on the shaft such that the shaft is rotatable relative to the sleeve and the sleeve is secured against displacements at least in a direction away from the cutting part, said mounting means comprising cooperating catch means present at the shaft and at the sleeve and which engage with one another, the annular duct being sealed relative to the surroundings of the tool and of the sleeve on its side facing the cutting part and on its opposite side solely by means of portions of the tool and of the sleeve, the sleeve comprising an axial, continuous bore having a widened portion and its end on the cutting part side and surrounds the tool, said tool comprising a shoulder on the side of the annular duct facing the cutting part, said shoulder being formed by an enlarged portion of the cutting part and being located inside the sleeve widened portion.

23. A device for the treatment of a bone or a tooth, comprising a tool and a sleeve, said tool being rotatable around an axis and comprising a cutting part, and a shaft connected to the cutting part, said sleeve being arranged on the shaft and together with the latter defining an annular duct for coolant, said sleeve comprising a coolant inlet opening into the duct, said tool comprising a passage extending from the duct to the cutting part, means for mounting the sleeve on the shaft such that the shaft is rotatable relative to the sleeve and the sleeve is secured against displacements at least in a direction away from the cutting part, said mounting means comprising cooperating catch means present at the shaft and at the sleeve and which engage with one another, the shaft comprising a single annular groove defining the annular duct and also constituting its catch means, said sleeve catch means being a rib configured to fill only part of said shaft groove.

* * * * *